"""" US009474702B2

(12) United States Patent
Shin et al.

(10) Patent No.: US 9,474,702 B2
(45) Date of Patent: *Oct. 25, 2016

(54) COSMETIC USE OF SALICYLIC ACID DERIVATIVES

(71) Applicant: Avon Products, Inc., Suffern, NY (US)

(72) Inventors: Sung Bin Shin, Mahwah, NJ (US); Hong Hu, Basking Ridge, NJ (US); Kai Xi, Whitehouse Station, NJ (US)

(73) Assignee: Avon Products, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/044,189

(22) Filed: Feb. 16, 2016

(65) Prior Publication Data

US 2016/0193127 A1 Jul. 7, 2016

Related U.S. Application Data

(63) Continuation of application No. 14/408,735, filed as application No. PCT/US2014/022988 on Mar. 11, 2014, now Pat. No. 9,289,363.

(60) Provisional application No. 61/778,610, filed on Mar. 13, 2013.

(51) Int. Cl.
| | | |
|---|---|---|
| *A61K 8/00* | (2006.01) | |
| *A61K 8/02* | (2006.01) | |
| *A61K 31/60* | (2006.01) | |
| *A61K 8/37* | (2006.01) | |
| *A61K 8/368* | (2006.01) | |
| *A61Q 19/00* | (2006.01) | |
| *A61Q 19/02* | (2006.01) | |
| *A61Q 19/08* | (2006.01) | |
| *A61K 8/36* | (2006.01) | |
| *A61Q 17/00* | (2006.01) | |
| *A61K 8/06* | (2006.01) | |
| *A61K 8/34* | (2006.01) | |
| *A61K 31/618* | (2006.01) | |
| *C12Q 1/37* | (2006.01) | |

(52) U.S. Cl.
CPC . *A61K 8/37* (2013.01); *A61K 8/06* (2013.01); *A61K 8/342* (2013.01); *A61K 8/361* (2013.01); *A61K 8/368* (2013.01); *A61K 31/60* (2013.01); *A61K 31/618* (2013.01); *A61Q 17/00* (2013.01); *A61Q 19/00* (2013.01); *A61Q 19/007* (2013.01); *A61Q 19/02* (2013.01); *A61Q 19/08* (2013.01); *C12Q 1/37* (2013.01); *A61K 2800/43* (2013.01); *A61K 2800/48* (2013.01); *A61K 2800/522* (2013.01); *A61K 2800/54* (2013.01); *A61K 2800/78* (2013.01)

(58) Field of Classification Search
None
See application file for complete search history.

(56) References Cited

U.S. PATENT DOCUMENTS

| | | | |
|---|---|---|---|
| 4,477,467 A | 10/1984 | Nishizawa | |
| 5,658,956 A | 8/1997 | Martin et al. | |
| 6,120,756 A * | 9/2000 | Markowitz | A61K 8/368 424/401 |
| 9,289,363 B2 * | 3/2016 | Shin | A61K 8/368 |
| 2009/0053290 A1 * | 2/2009 | Sand | A61K 8/34 424/449 |
| 2012/0087872 A1 | 4/2012 | Tamarkin et al. | |

FOREIGN PATENT DOCUMENTS

| | | |
|---|---|---|
| EP | 0970690 A1 | 1/2000 |
| GB | 177411 A | 1/1970 |
| WO | 7900556 A1 | 8/1979 |

OTHER PUBLICATIONS

Yousef et al.; Cancer Research 63, 3958-3965, Jul. 15, 2003.*
Yoon et al.; J. Biol. Chem.; vol. 282, No. 44, pp. 31852-31864; Nov. 2, 2007.*
Pubchem CID 17200269, pp. 1-3 <URL: http://pubchem.ncbi.nlm.nih.gov/summary.cgi?cid=17200269&loc=ec_res> (2007).
Pubchem CID 23011370, pp. 1-3 <URL: http://pubchem.ncbi.nlm.nih.gov/summary.cgi?cid=23011370&loc=ec_res> (2007).
Sinko et al., "Skin-PAMPA: A new method for fast prediction of skin penetration," European Journal of Pharmaceutical Sciences, vol. 45, pp. 698-707 (2012).
Mitra et al., "Photophysical properties of substituted intramolecularly hydrogen bonded compounds: A combined experimental and theoretical study," Journal of Luminescence, vol. 118, pp. 1-11 (2006).

* cited by examiner

*Primary Examiner* — Jeffrey T Palenik
(74) *Attorney, Agent, or Firm* — Jonathan D. Ball; Greenberg Traurig, LLP

(57) ABSTRACT

Cosmetic compositions comprising salicylic acid dimers and methods of using such compositions to impart anti-aging benefits to the skin are disclosed. The salicylic acid derivatives are believed to have modulatory activity against one or more biochemical pathways implicated in the appearance of human skin.

17 Claims, 1 Drawing Sheet

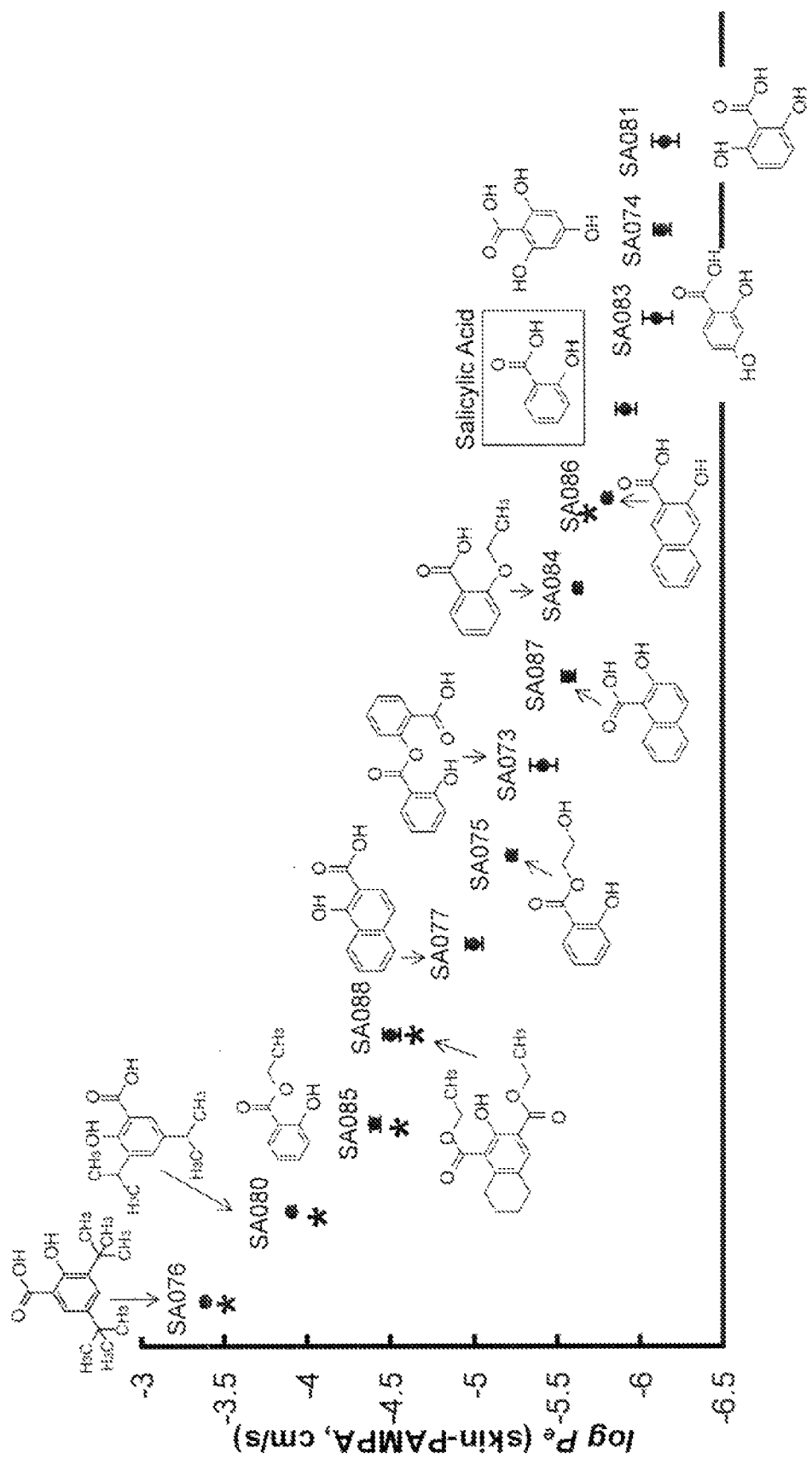

COSMETIC USE OF SALICYLIC ACID DERIVATIVES

CROSS-REFERENCE TO RELATED APPLICATIONS

This application is a continuation of U.S. Nonprovisional patent application Ser. No. 14/408,735 filed on Dec. 17, 2014, which is a national stage application of and claims priority to US PCT Application Serial No. PCT/US14/23063 filed Mar. 11, 2014, which claims priority benefit to U.S. Provisional Patent Application Ser. No. 61/778,610, filed on Mar. 13, 2013, the entirety of each of which is herein incorporated by reference for all purposes and priority to each of which is claimed.

FIELD OF INVENTION

The present invention relates generally to compositions for topical application to the skin which comprise salicylic acid dimer and the use of such compositions to improve the aesthetic appearance of the skin.

BACKGROUND OF THE INVENTION

Salicylic acid (ortho-hydroxybenzoic acid) is found in the bark of the willow tree, *Salix alba*, and is also available synthetically. Salicylic acid as a topical agent has been used to treat a wide variety of skin disorders, most notably acne. It has been used as an exfoliant or keratolytic agent, and in the treatment of wrinkles and fine lines, skin pigmentation, dandruff, seborrheic dermatitis, acne, ringworm infection, psoriasis, calluses, ichthyosis, warts, and to reduce hyperpigmentation (e.g., age spots and freckles), and to improve the overall aesthetic appearance of skin. Salicylic acid is not without its drawbacks, however. For example, in some individuals, irritation and excessive drying of the skin may result.

It is therefore an object of the invention to provide new compositions and methods for improving the appearance of skin, combatting signs of intrinsic and photoaging, and/or treating skin disorders. It is a further object of the invention to provide compositions and methods for treating, reversing, forestalling and/or ameliorating skin wrinkles and fine lines with cosmetic compositions comprising effective amounts of a salicylic acid derivative. It is a further object of the invention to provide compositions and methods for treating, reversing, forestalling and/or ameliorating hyperpigmentation and other unwanted pigmentation in the skin with cosmetic compositions comprising effective amounts of a salicylic acid derivative. It is yet another object of the invention to provide compositions and methods for promoting exfoliation of the skin with effective amounts of a salicylic acid derivative.

The foregoing discussion is presented solely to provide a better understanding of nature of the problems confronting the art and should not be construed in any way as an admission as to prior art nor should the citation of any reference herein be construed as an admission that such reference constitutes "prior art" to the instant application.

SUMMARY OF THE INVENTION

In accordance with the foregoing objectives and others, it has surprisingly been found that salicylic acid dimer is a potent KLK5 stimulator and thus is contemplated to improve the aesthetic appearance of skin. Salicylic acid dimer is contemplated to be beneficial in treating signs of intrinsic aging and photo-aging of skin, skin hyperpigmentation, and skin disorders such as acne and blemishes, including those indications for which salicylic acid is conventionally used, and others.

In one aspect of the invention, cosmetic compositions are provided for improving the aesthetic appearance of skin comprising, in a cosmetically acceptable vehicle, an effective amount of salicylic acid dimer having the structure of formula (I):

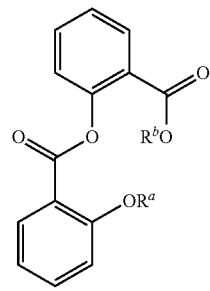

(I)

where $R^a$ and $R^b$ are independently selected from hydrogen or $C_1$-$C_{12}$ or $C_1$-$C_{10}$ or $C_1$-$C_8$ or $C_1$-$C_6$ or $C_1$-$C_4$ branched, straight chained or cyclic hydrocarbons, optionally substituted with 1-4 (i.e., one, two, three, or four) heteroatoms selected from halogen, oxygen, nitrogen, and sulfur; and cosmetically acceptable salts and esters thereof.

In certain implementations, the compound of Formula (I) may exist as a diacid where $R^a$ and $R^b$ are each hydrogen. In other embodiments, the mono- and di-esters are also contemplated to be suitable. The esters may be, for example, methyl, ethyl, propyl, butyl, pentyl, or hexyl esters. In certain implementations, the compound is an ethyl monoester where either $R^a$ or $R^b$ is ethyl. In certain implementations, the compound is an ethyl diester where both $R^a$ or $R^b$ are ethyl.

In one aspect of the invention, a method is provided for improving the aesthetic appearance of human skin comprising topically applying to an area of the skin in need thereof an effective amount of salicylic acid dimer according to Formula (I) or a cosmetically acceptable salt thereof in a cosmetically acceptable vehicle. The compound may be administered daily for a period of time sufficient to improve the aesthetic appearance of the skin.

In a related aspect, a method is provided for reducing blemishes or acne in human skin comprising topically applying to skin in need thereof an effective amount of salicylic acid dimer according to Formula (I) or a cosmetically acceptable salt thereof for a time sufficient to improve the aesthetic appearance of said blemish or acne.

Also provided is a method for promoting exfoliation of human skin comprising topically applying an area of skin in need thereof an effective amount of salicylic acid dimer according to Formula (I) or a cosmetically acceptable salt thereof for a time sufficient to promote exfoliation.

Additionally, a method is provided for treating one or more signs of skin aging comprising topically applying to skin in need an effective amount of salicylic acid dimer according to Formula (I) or a cosmetically acceptable salt thereof, for a time sufficient to improve the signs of skin aging.

In yet another aspect, a method is provided for treating hyperpigmentation or otherwise reducing unwanted pigmentation in the skin comprising topically applying to skin in need thereof an effective amount of salicylic acid dimer according to Formula (I) or a cosmetically acceptable salt thereof, for a time sufficient to improve the signs of skin aging.

These and other aspects of the present invention will be better understood by reference to the following detailed description and appended claims.

BRIEF DESCRIPTION OF THE FIGURES

FIG. 1. shows permeability data of several salicylic acid derivatives relative to salicylic acid. The asterisk (*) indicates salicylic acid derivatives that have higher KLK5 activity relative to salicylic acid.

DETAILED DESCRIPTION

All terms used herein are intended to have their ordinary meaning unless otherwise provided. All ingredient amounts provided herein are by weight percent of the total composition unless otherwise indicated. As used herein, the term "consisting essentially of" is intended to limit the invention to the specified materials or steps and those that do not materially affect the basic and novel characteristics of the claimed invention, as understood from a reading of this specification.

The present invention provides compositions for topical application to the human integumentary system, including without limitations skin, nails, hair, etc. The site of application to skin may be skin of the face, lips, hands, chest, etc. The compositions comprise an effective amount of a salicylic acid derivative to treat, reverse, ameliorate, forestall, and/or prevent signs of skin aging or otherwise improve the aesthetic appearance of human skin.

Without wishing to be bound by any particular theory, it is believed that the compositions of the present invention stimulate the enzyme KLK5, a serine protease expressed in the epidermis. KLK5 degrades proteins which form the extracellular component of cell junctions in the stratum corneum and may be involved in the regulation of desquamation.

The cosmetic compositions for improving the aesthetic appearance of human skin comprise, in a cosmetically acceptable vehicle, an amount of a salicylic acid dimer effective to improve the aesthetic appearance of skin. These salicylic acid dimers may have the structure of formula (I):

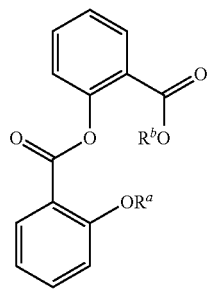

(I)

where $R^a$ and $R^b$ are independently selected from hydrogen or $C_1$-$C_{12}$ or $C_1$-$C_{10}$ or $C_1$-$C_8$ or $C_1$-$C_6$ or $C_1$-$C_4$ branched, straight chained or cyclic hydrocarbons, optionally substituted with 1-4 (i.e., one, two, three, or four) heteroatoms selected from halogen, oxygen, nitrogen, and sulfur; including without limitation methyl, ethyl, propyl, butyl, pentyl, and hexyl;

In some embodiments, $R^a$ and $R^b$ are may independently be selected from hydrogen or lower alkyl, e.g., methyl, ethyl, propyl, butyl, pentyl, and hexyl. In certain implementations, $R^a$ and $R^b$ are both methyl. In certain implementations, $R^a$ and $R^b$ are both ethyl. In certain implementations, $R^a$ and $R^b$ are both propyl. In certain implementations, $R^a$ and $R^b$ are both butyl. In each case, the lower alkyl may have a subsistent R, such as a hydroxyl group or halogen, or the lower alkyl may comprise one or more (e.g., from 1-4) oxa or oxo substituents. In some embodiments, $R^a$ and $R^b$ are each hydrogen and the compound has the structure of Formula (Ia):

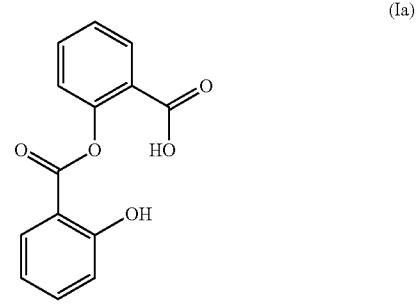 [SMILES: O=C(Oc1ccccc1C(=O)O)c1ccccc1O]

(Ia)

The cosmetic compositions according to the invention can be formulated in a variety of forms for topical application and will comprise from about 0.00001% by weight to about 90% by weight of one or more compounds according to Formulas (I) or (Ia), and preferably will comprise from about 0.0001% by weight to about 25% by weight, and more preferably from about 0.001% by weight to about 1% by weight of the composition. In one embodiment, the active will comprise from about 0.01% by weight to about 0.1% by weight or to 0.5% by weight of the composition. In another embodiment, the active will comprise from about 0.001% by weight to about 5% by weight of the composition. The compositions will comprise and effective amount of the salicylic acid derivative compounds according to Formulas (I) or (Ia), by which is meant an amount sufficient to have a keratolytic effect in a given area of skin when topically applied thereto.

The composition may be formulated in a variety of product forms, such as, for example, a lotion, cream, serum, spray, aerosol, cake, ointment, essence, gel, paste, patch, pencil, towelette, mask, stick, foam, elixir, concentrate, and the like, particularly for topical administration. Preferably the composition is formulated as a lotion, cream, ointment, or gel.

The cosmetically acceptable vehicle may be in the form of an emulsion. Non-limiting examples of suitable emulsions include water-in-oil emulsions, oil-in-water emulsions, silicone-in-water emulsions, water-in-silicone emulsions, wax-in-water emulsions, water-oil-water triple emulsions or the like having the appearance of a cream, gel or microemulsions. The emulsion may include an emulsifier, such as a nonionic, anionic or amphoteric surfactant, typically in an amount from about 0.001% to about 5% by weight.

The cosmetically acceptable vehicle may include water; vegetable oils; mineral oils; esters such as octal palmitate, isopropyl myristate and isopropyl palmitate; ethers such as dicapryl ether and dimethyl isosorbide; alcohols such as ethanol and isopropanol; fatty alcohols such as cetyl alcohol, cetearyl alcohol, stearyl alcohol and biphenyl alcohol; isoparaffins such as isooctane, isododecane and is hexadecane; silicone oils such as cyclomethicone, dimethicone, dimethicone cross-polymer, polysiloxanes and their derivatives, preferably organomodified derivatives; hydrocarbon oils such as mineral oil, petrolatum, isoeicosane and polyisobutene; polyols such as propylene glycol, glycerin, butylene glycol, pentylene glycol and hexylene glycol; waxes such as beeswax and botanical waxes; or any combinations or mixtures of the foregoing. Aqueous vehicles may include one or more solvents miscible with water, including lower alcohols, such as ethanol, isopropanol, and the like.

In one embodiment of the invention, the compositions may include additional skin actives such as, but are not limited to, botanicals, other keratolytic agents, desquamating agents, keratinocyte proliferation enhancers, collagenase inhibitors, elastase inhibitors, depigmenting agents, anti-inflammatory agents, steroids, anti-acne agents, antioxidants, thiodipropionic acid or esters thereof, and advanced glycation end-product (AGE) inhibitors. Exemplary anti-aging components include, without limitation, botanicals (e.g., *Butea Frondosa* extract); thiodipropionic acid (TDPA) and esters thereof; retinoids (e.g., all-trans retinoic acid, 9-cis retinoic acid, phytanic acid and others); hydroxy acids (including alpha-hydroxyacids and beta-hydroxyacids), salicylic acid and salicylates; other exfoliating agents (e.g., glycolic acid, 3,6,9-trioxaundecanedioic acid, etc.), estrogen synthetase stimulating compounds (e.g., caffeine and derivatives); compounds capable of inhibiting 5 alpha-reductase activity (e.g., linolenic acid, linoleic acid, finasteride, and mixtures thereof); barrier function enhancing agents (e.g., ceramides, glycerides, cholesterol and its esters, alpha-hydroxy and omega-hydroxy fatty acids and esters thereof, etc.); collagenase inhibitors; and elastase inhibitors; to name a few. In one embodiment, the composition comprises N-Acetyl Tyrosinamide.

Exemplary retinoids include, without limitation, retinoic acid (e.g., all-trans or 13-cis), and derivatives thereof, retinaldehyde, retinol (Vitamin A) and esters thereof, such as retinol palmitate, retinol acetate and retinol propionate, and salts thereof. Particular mention may be made of retinol. It is contemplated that combinations of the compounds of Formulas (I) or (Ia) with any of these retinoids will provide enhanced or synergistic improvements to skin. The retinoids will typically be included in amounts from about 0.0001% to about 5% by weight, more typically from about 0.01% to about 2.5% by weight or from about 0.1% to about 1.0% by weight. Compositions according to this embodiment will typically include an antioxidant such as ascorbic acid and/or BHT and/or a chelating agent such as EDTA or a salt thereof.

In another embodiment, the topical compositions of the present invention may also include one or more of the following: a skin penetration enhancer, an emollient, a humectant, a skin plumper, an optical diffuser, a sunscreen, an additional exfoliating agent, an antioxidant, and a pH adjuster.

An emollient provides the functional benefits of enhancing skin smoothness and reducing the appearance of fine lines and coarse wrinkles. Examples include isopropyl myristate, petrolatum, isopropyl lanolate, silicones (e.g., methicone, dimethicone), oils, mineral oils, fatty acid esters, or any mixtures thereof. The emollient may be preferably present from about 0.1 wt % to about 50 wt % of the total weight of the composition.

A skin plumper serves as a collagen enhancer to the skin. An example of a suitable, and preferred, skin plumper is palmitoyl oligopeptide. Other skin plumpers are collagen and/or other glycosaminoglycan (GAG) enhancing agents. When present, the skin plumper may comprise from about 0.1 wt % to about 20 wt % of the total weight of the composition.

A sunscreen for protecting the skin from damaging ultraviolet rays may also be included. Preferred sunscreens are those with a broad range of UVB and UVA protection, such as octocrylene, avobenzone (Parsol 1789), octyl methoxycinnamate, octyl salicylate, oxybenzone, homosylate, benzophenone, camphor derivatives, zinc oxide, and titanium dioxide. When present, the sunscreen may comprise from about 0.01 wt % to about 70 wt % of the composition.

Suitable exfoliating agents include, for example, alpha-hydroxyacids, beta-hydroxyacids, oxaacids, oxadiacids, and their derivatives such as esters, anhydrides and salts thereof. Suitable hydroxy acids include, for example, glycolic acid, lactic acid, malic acid, tartaric acid, citric acid, 2-hydroxyalkanoic acid, mandelic acid, salicylic acid and other derivatives thereof (other than those of the invention). A preferred exfoliating agent is glycolic acid. When present, the exfoliating agent may comprise from about 0.1 wt % to about 80 wt % of the composition.

An antioxidant functions, among other things, to scavenge free radicals from skin to protect the skin from environmental aggressors. Examples of antioxidants that may be used in the present compositions include compounds having phenolic hydroxy functions, such as ascorbic acid and its derivatives/esters; beta-carotene; catechins; curcumin; ferulic acid derivatives (e.g., ethyl ferulate, sodium ferulate); gallic acid derivatives (e.g., propyl gallate); lycopene; reductic acid; rosmarinic acid; tannic acid; tetrahydrocurcumin; tocopherol and its derivatives; uric acid; or any mixtures thereof. Other suitable antioxidants are those that have one or more thiol functions (—SH), in either reduced or non-reduced form, such as glutathione, lipoic acid, thioglycolic acid, and other sulfhydryl compounds. The antioxidant may be inorganic, such as bisulfites, metabisulfites, sulfites, or other inorganic salts and acids containing sulfur. In one particular embodiment, the inventive compositions will include TDPA or an ester thereof (e.g., dilauryl thiodipropionic acid), and/or an alpha hydroxyl acid (glycolic acid) and/or beta hydroxyl acid (salicylic acid or a derivative). Compositions of the present invention may comprise an antioxidant, which may comprise from about 0.001 wt % to about 10 wt %, or from about 0.01 wt % to about 5 wt %, of the total weight of the composition.

Other conventional additives include: vitamins, such as tocopherol and ascorbic acid; vitamin derivatives such as ascorbyl monopalmitate; thickeners such as hydroxyalkyl cellulose; gelling agents; structuring agents; metal chelating agents such as EDTA or salts thereof pigments; colorants; and pH adjusters. The composition may optionally comprise other components known to those skilled in the art including, but not limited to, film formers, moisturizers, minerals, viscosity and/or rheology modifiers, anti-acne agents, insect repellents, skin cooling compounds, skin protectants, lubricants, fragrances, preservatives, stabilizers, and mixtures thereof. In addition to the foregoing, the cosmetic compositions of the invention may contain any other compound for the treatment of skin disorders. The conventional additives, actives, adjuvants, and excipients set forth in the preceding paragraphs are present in the compositions in amounts suitable to obtain their intended purpose and effect, each typically being present in an amount of from 0.01 to 25% by weight of the cosmetic composition, in particular from about 0.1 to 5% by weight of the cosmetic composition.

The compositions may include liposomes. The liposomes may comprise other additives or substances and/or may be modified to more specifically reach or remain at a site following administration.

In one embodiment, the composition of the invention comprising a salicylic acid derivative may have a pH between about 1 and about 8. In certain embodiments, the pH of the composition will be acidic, i.e., less than 7.0, and preferably will be between about 2 and about 7, more preferably between about 3.5 and about 5.5.

The compositions are applied to the skin for a period of time sufficient to diminish the appearance of melanin in the skin. The compositions may be applied topically once, twice, or more daily. The treatment may be for a period of one week, two weeks, four weeks, eight weeks, or more. In one embodiment, the compositions of the invention will be applied to the skin in an amount from about 0.001 to about 100 mg/cm$^2$, more typically from about 0.01 to about 20 mg/cm$^2$, or from about 0.1 to about 10 mg/cm$^2$. When the cosmetic compositions according to the invention are formulated in a liquid form, they typically will contained the salicylic acid derivatives at a concentration from about 0.001 μM to about 50 μM, or from about 0.5 μM to about 10 μM, or from about 2.25 μM to about 10 μM.

The invention provides a method for treating aging skin by topically applying a composition comprising a salicylic acid derivative, preferably in a cosmetically acceptable vehicle, over the affected area for a period of time sufficient to reduce, ameliorate, reverse or prevent dermatological signs of aging. This method is particularly useful for treating signs of skin photoaging and intrinsic aging.

Generally, the improvement in the condition and/or aesthetic appearance is selected from the group consisting of: reducing dermatological signs of chronological aging, photo-aging, hormonal aging, and/or actinic aging; preventing and/or reducing the appearance of lines and/or wrinkles; reducing the noticeability of facial lines and wrinkles, facial wrinkles on the cheeks, forehead, perpendicular wrinkles between the eyes, horizontal wrinkles above the eyes, and around the mouth, marionette lines, and particularly deep wrinkles or creases; preventing, reducing, and/or diminishing the appearance and/or depth of lines and/or wrinkles; improving the appearance of suborbital lines and/or periorbital lines; reducing the appearance of crow's feet; rejuvenating and/or revitalizing skin, particularly aging skin; reducing skin fragility; preventing and/or reversing of loss of glycosaminoglycans and/or collagen; ameliorating the effects of estrogen imbalance; preventing skin atrophy; preventing, reducing, and/or treating hyperpigmentation; minimizing skin discoloration; improving skin tone, radiance, clarity and/or tautness; preventing, reducing, and/or ameliorating skin sagging; improving skin firmness, plumpness, suppleness and/or softness; improving procollagen and/or collagen production; improving skin texture and/or promoting retexturization; improving skin barrier repair and/or function; improving the appearance of skin contours; restoring skin luster and/or brightness; minimizing dermatological signs of fatigue and/or stress; resisting environmental stress; replenishing ingredients in the skin decreased by aging and/or menopause; improving communication among skin cells; increasing cell proliferation and/or multiplication; increasing skin cell metabolism decreased by aging and/or menopause; retarding cellular aging; improving skin moisturization; enhancing skin thickness; increasing skin elasticity and/or resiliency; enhancing exfoliation; improving microcirculation; decreasing and/or preventing cellulite formation; and any combinations thereof.

The composition will typically be applied to the skin one, two, or three times daily for as long as is necessary to achieve desired anti-aging results. The treatment regiment may comprise daily application for at least one week, at least two weeks, at least four weeks, at least eight weeks, or at least twelve weeks. Chronic treatment regimens are also contemplated.

The aesthetic improvement of human skin achieved with the compounds of Formulas (I) or (Ia) may include, without limitation, one or more of the following:

(a) treatment, reduction, and/or prevention of fine lines or wrinkles;
(b) reduction of skin pore size;
(c) improvement in skin thickness, plumpness, and/or tautness;
(d) improvement in skin smoothness, suppleness and/or softness;
(e) improvement in skin tone, radiance, and/or clarity;
(f) improvement in procollagen, and/or collagen production;
(g) improvement in maintenance and remodeling of elastin;
(h) improvement in skin texture and/or promotion of retexturization;
(i) improvement in skin barrier repair and/or function;
(j) improvement in appearance of skin contours;
(k) restoration of skin luster and/or brightness;
(l) replenishment of essential nutrients and/or constituents in the skin;
(m) improvement of skin appearance decreased by aging and/or menopause;
(n) improvement in skin moisturization;
(o) increase in skin elasticity and/or resiliency;
(p) treatment, reduction, and/or prevention of skin sagging;
(q) improvement in skin firmness; and
(r) reduction of pigment spots and/or mottled skin; and
(s) improvement of optical properties of skin by light diffraction or reflection.

In practice, the compositions of the invention according to Formulas (I) or (Ia) are applied to skin in need of treatment. That is, skin which suffers from a deficiency or loss in any of the foregoing attributes or which would otherwise benefit from improvement in any of the foregoing skin attributes.

In certain preferred embodiments the compositions and methods of the invention are directed to the prevention, treatment, and/or amelioration of fine lines and/or wrinkles in the skin. In this case, the compositions are applied to skin in need of treatment, by which is meant skin having wrinkles and/or fine lines. Preferably, the compositions are applied directly to the fine lines and/or wrinkles. The compositions and methods are suitable for treating fine lines and/or wrinkles on any surface of the skin, including without limitation, the skin of the face, neck, and/or hands.

In other preferred embodiments, the compositions and methods of the invention are directed to the prevention, treatment, and/or amelioration of blemishes, acne, or hyperpigmentation in human skin. In this case, the compositions are applied to skin in need of treatment, by which is meant skin having a blemish, acne, or hyperpigmentation. The compositions may be applied directly to the blemish, acne, or area of the skin that is hyperpigmented (e.g., age spots or freckles).

In other preferred embodiments, the compositions and methods of the invention are directed to promoting exfoliation of human skin. In this case, the compositions are applied to skin in need of treatment, by which is meant skin in need of exfoliation. The compositions may be applied directly to the area of skin in need of exfoliation.

In other embodiments, the salicylic acid derivatives of the invention may be used to treat, prevent, or ameliorate skin pigmentation, dandruff, seborrheic dermatitis, ringworm infection, psoriasis, calluses, ichthyosis, and warts.

The salicylic acid derivative component is topically applied to an "individual in need thereof," by which is meant an individual that stands to benefits from reducing visible signs of skin damage or aging. In a specific embodiment, the salicylic acid derivative component is provided in a pharmaceutically, physiologically, cosmetically, and dermatologically-acceptable vehicle, diluent, or carrier, where the composition is topically applied to an affected area of skin and left to remain on the affected area in an amount effective for improving the condition and aesthetic appearance of skin.

In one embodiment, methods for treating and improving the signs of skin aging (e.g., fine lines and wrinkles), methods for reducing blemishes or acne, and methods for promoting exfoliation of skin comprise topically applying the inventive salicylic acid derivative compositions to the skin of an individual in need thereof (e.g., topical application directly to the fine line and/or wrinkle, to the blemish or acne, to the area of skin in need of exfoliation) in an amount and for a time sufficient to reduce the severity of the fine lines and/or wrinkles, to reduce the blemish or acne, or to promote exfoliation, or to prevent or inhibit the formation of new fine lines and/or wrinkles, the formation of acne or a blemish, or to prevent the need for additional exfoliation.

The effect of a composition on the formation or appearance of fine lines and wrinkles, of a blemish or of acne can be evaluated qualitatively, e.g., by visual inspection, or quantitatively, e.g., by microscopic or computer assisted measurements of wrinkle morphology (e.g., the number, depth, length, area, volume and/or width of wrinkles per unit area of skin). This embodiment includes treatment of wrinkles, blemishes, or acne, and promoting exfoliation on the skin of the hands, arms, legs, neck, chest, and face, including the forehead, It is also contemplated that the compositions of the invention will be useful for treating thin skin by topically applying the composition to thin skin of an individual in need thereof "Thin skin" is intended to include skin that is thinned due to chronological aging, menopause, or photodamage. In some embodiments, the treatment is for thin skin in men, whereas other embodiments treat thin skin in women, pre-menopausal or post-menopausal, as it is believed that skin thins differently with age in men and women, and in particular in women at different stages of life.

The methods of the invention may be employed prophylactically to forestall aging including in patients that have not manifested signs of skin aging, most commonly in individuals under 25 years of age. The methods may also reverse or treat signs of aging once manifested as is common in individuals over 25 years of age. The methods of the invention may also be used in individuals either under 25 years of age or 25 years of age or older, to prevent, reverse, or treat acne, blemishes, hyperpigmentation, to improve the aesthetic appearance of skin, or to promote exfoliation of skin.

The following examples are meant to demonstrate certain aspects of the invention in a non-limiting fashion.

EXAMPLES

Example 1

The compound of Formula 1a was assayed for enzymatic activity of Kallikrein 5 (KLK5) as follows, and its activity compared to that of salicylic acid. The KLK5 activity of the compound of Formula 1a was calculated as a percentage of KLK5 activity relative to salicylic acid.

In the stratum corneum, skin's outermost layer, cell-to-cell cohesion depends primarily on proteins known as the corneodesmosomes. During skin remodeling and renewal dead cells are shed from the skin surface by the action of native proteases that break down the corneodesmosomes. Human tissue Kallikreins (KLKs) are a family of proteases that reside in the stratum corneum and were shown to be directly involved in corneodesmosome turnover. Hypothetically, up-regulation of the activities of these proteases using different active candidates could be utilized to increase the rate of shedding of dead skin, thus providing a natural means for skin exfoliation. To this end, the enzymatic activity of a member of the KLK family, recombinant human (rh) KLK5, was monitored following pre-incubation with actives and measuring the rate of peptide bond cleavage of a synthetic substrate.

Enzymatic activity of KLK5 was measured by incubating recombinant human (rh) KLK5 protease (R&D Systems, Cat No. 1108-SE) with a specific fluorogenic peptide substrate Boc-V-P-R-AMC (R&D Systems, Cat No. ES011). The substrate is conjugated to a quenched fluorescent group. Upon cleavage of the adjacent peptide bond, the fluorescent signal is released, resulting in a measurable emission at 535 nm when excited at 340 nm wavelength. Increase in fluorescence reading indicates an increase in rhKLK5 activity. The test compounds were reacted with recombinant rhKLK5 protease for 60 seconds followed by addition of Boc-V-P-R-AMC Fluorogenic Peptide Substrate. After 60 seconds of incubation, fluorescence was measured at 340 nm (Excitation wavelength) and 485 nm (Emission wavelength) every 1 minute for 7 minutes. Rate (kinetics) of enzyme activity was calculated as follows: Rate of enzyme activity=Change of fluorescent reading (after background correction)/Change of reaction time (min). Percent change of activity due to a test compound was calculated by comparing rate of enzyme activity in the presence of the test compound to that of a control without the test compound and statistical significance was calculated using a t-test. Additionally, the rate of activity of the compounds was compared to that of salicylic acid.

Relative to salicylic acid, the results show that the dimer (compound of Formula 1a) achieved about 90% of the stimulator effect of salicylic acid, although that difference was not significant. Because the molecular weight of the dimer is essentially twice that of the salicylic acid, it will be observed that the dimer was tested at a concentration approximately half of that of the salicylic acid. Despite the far lower concentration, the potency of the dimer relative to the salicylic acid was not significantly less. The dimer showed about 90% of the potency of salicylic acid in the KLK5 assay.

Results illustrate that the dimer (compound of Formula 1a) is a potent stimulator of KLK5. This dimer is believed to be potent keratolytic agent due to its effects on the enzyme KLK5 relative to salicylic acid, and is thereby contemplated to have beneficial effects on skin, including without limitation, reducing one or more signs of skin aging, improving the aesthetic appearance of skin, reducing acne or blemishes, reducing hyperpigmentation, and promoting exfoliation of the skin.

Example 2

Several salicylic acid derivatives were assessed for their ability to penetrate skin. The chemical structure of each of the compounds tested along with an alphanumeric identifier is shown in FIG. 1. Each of the compounds was formulated in an aqueous buffer, with a final pH of 4.25 at a concentration of 50 μM. The skin permeability of the compounds was measured using a high throughput transdermal permeability model, the parallel artificial membrane penetration assay (Skin PAMPA™), which uses a skin mimetic artificial membrane that simulates the barrier properties of the strateum corneum.

Briefly, the Skin PAMPA™ assay is a sandwich assay that utilizes two 96-well plate assemblies, one of which acts as the acceptor chambers (comprising a buffer), and one of which acts as the donor chambers (comprising a buffer and the compound to be tested). Between the two chambers is a skin mimetic artificial membrane, which is a 125 μm thick microfilter disc (with 0.45 μm pores) that is coated with a skin-mimetic lipid mixture (Pion, Inc.). After an incubation period, the donor and acceptor chambers are analyzed for the amount of compound present.

In the current experiments, the acceptor chamber included an acceptor solution made from Prisma™ HT buffer solution (Pion, Inc.) that was adjusted to a pH of 7.4±0.05 using 1.0 M NaOH, and the donor chamber included a donor solution made from Prisma™ HT buffer solution (Pion, Inc.) that was adjusted to a pH of 4.25±0.05 using 1.0 M NaOH. The donor solution in the different donor chambers also contained solutions of the salicylic acid derivatives tested. Once the PAMPA sandwich was assembled, it was allowed to incubate for two hours. After incubation, the sandwich was separated, and equal amounts of the donor and receiver chambers were assayed for the amount of salicylic acid derivative present by measuring UV absorption and comparing the values with the UV spectrum obtained from reference standards. Mass balance was used to determine the amount of material remaining in the membrane filter, and on the plastic of the chambers. Effective permeability was then calculated by the same method as Sinko et al., Eur. J. Pharm. Sci. 11; 45(5):698-707 (2012), the disclosure of which is hereby incorporated by reference in its entirety. As shown in FIG. 1, the different salicylic acid derivatives assessed have varying degrees of skin permeability, the majority of which have greater skin permeability than salicylic acid.

In addition, each of the salicylic acid derivatives tested for skin permeability was assayed for enzymatic activity of KLK5 in the manner described in Example 1, and their activity compared to that of salicylic acid. The compounds having enzymatic activity of KLK5 greater than salicylic acid are indicated with an asterisk in FIG. 1. As shown, several of the salicylic acid derivatives that are highly skin permeable are potent stimulators of KLK, with greater KLK5 enzymatic activity than salicylic acid.

The salicylic acid derivatives shown in FIG. 1 are believed to be potent keratolytic agents by their ability to stimulate the enzyme KLK5, and are thereby contemplated to have beneficial effects on skin, including without limitation, reducing one or more signs of skin aging, improving the aesthetic appearance of skin, reducing acne or blemishes, reducing hyperpigmentation, and promoting exfoliation of the skin. It should be understood that each compound in FIG. 1, with the exception of salicylic acid, is considered to be useful and thus each comprise an embodiment of the invention for improving the appearance of skin. Any of these compounds can be used in any of the methods described herein and/or included in any of the formulations described.

All references including patent applications and publications cited herein are incorporated herein by reference in their entirety and for all purposes to the same extent as if each individual publication or patent or patent application was specifically and individually indicated to be incorporated by reference in its entirety for all purposes. Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

The invention claimed is:

1. A cosmetic composition comprising, in a cosmetically acceptable vehicle, an effective amount of a salicylic acid derivative having the structure of formula (I):

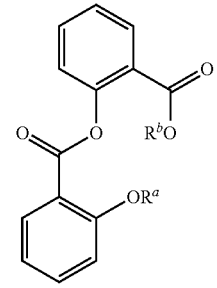

where $R^a$ and $R^b$ are independently selected from hydrogen or $C_1$-$C_{12}$ branched, straight chained or cyclic hydrocarbons, optionally substituted with 1-4 heteroatoms selected from halogen, oxygen, nitrogen, and sulfur;

and cosmetically acceptable salts thereof wherein said effective amount is between about 0.001% by weight to about 5% by weight based on the total weight of the composition.

2. The cosmetic composition according to claim 1, wherein $R^a$ and $R^b$ are independently selected from hydrogen, methyl, ethyl, propyl, butyl, pentyl, and hexyl.

3. The cosmetic composition according to claim 1, wherein $R^a$ and $R^b$ are both ethyl.

4. The cosmetic composition according to claim 1, wherein $R^a$ and $R^b$ are both hydrogen.

5. The composition according to claim 1, wherein said cosmetically acceptable vehicle comprises a water-in-oil, oil-in-water, silicone-in-water, or water-in-silicone emulsion and further comprises an emulsifier.

6. The composition according to claim 1, further comprising a retinoid selected from the group consisting of retinoic acid, retinol, retinal, retinyl acetate, and retinyl palmitate.

7. The cosmetic composition according to claim 1, further comprising a cosmetic ingredient selected from a film forming polymer, a thickener, a pH adjuster, a preservative, an emulsifier, a gelling agent, an antioxidant, an emollient, a humectant, a fragrance, and a colorant.

8. A method for improving the aesthetic appearance of human skin comprising topically applying to an area of the skin in need thereof a composition according to claim 1, for a time sufficient to improve the aesthetic appearance of said human skin.

9. The method according to claim 8, wherein said aesthetic improvement of said human skin is selected from the group consisting of:

(a) treatment, reduction, and/or prevention of fine lines or wrinkles;
(b) reduction of skin pore size;
(c) improvement in skin thickness, plumpness, and/or tautness;
(d) improvement in skin smoothness, suppleness and/or softness;
(e) improvement in skin tone, radiance, and/or clarity;
(f) improvement in procollagen, and/or collagen production;
(g) improvement in maintenance and remodeling of elastin;
(h) improvement in skin texture and/or promotion of retexturization;
(i) improvement in skin barrier repair and/or function;
(j) improvement in appearance of skin contours;
(k) restoration of skin luster and/or brightness;
(l) replenishment of essential nutrients and/or constituents in the skin;
(m) improvement of skin appearance decreased by aging and/or menopause;
(n) improvement in skin moisturization;
(o) increase in skin elasticity and/or resiliency;
(p) treatment, reduction, and/or prevention of skin sagging;
(q) improvement in skin firmness; and
(r) reduction of pigment spots and/or mottled skin; and
(s) improvement of optical properties of skin by light diffraction or reflection.

10. The method according to claim 9, wherein said composition is applied at least once daily for a period of at least four weeks.

11. A method for reducing blemishes or acne in human skin comprising topically applying to an area of the skin in need thereof a composition according to claim 1, for a time sufficient to improve the aesthetic appearance of said blemish or acne.

12. A method for promoting exfoliation of human skin comprising topically applying to an area of the skin in need thereof a composition according to claim 1.

13. A cosmetic composition comprising, in a cosmetically acceptable vehicle, an effective amount of a salicylic acid derivative having the structure:

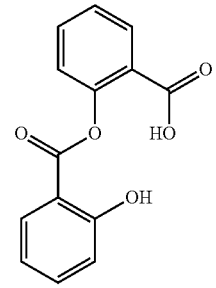 [SMILES: O=C(Oc1ccccc1C(=O)O)c1ccccc1O]

and cosmetically acceptable salts thereof, wherein said effective amount is from about 0.001% and about 5% by weight.

14. A method of improving the aesthetic appearance of skin comprising topically apply to said skin the composition of claim 13.

15. The composition according to claim 13, further comprising a retinoid selected from the group consisting of retinoic acid, retinol, retinal, retinyl acetate, and retinyl palmitate.

16. The composition according to claim 1, further comprising a retinoid selected from the group consisting of retinoic acid, retinol, retinal, retinyl acetate, and retinyl palmitate.

17. A method of screening for dermatologically active substances comprising contacting KLK5 protease with a peptide substrate for KLK5 protease in the presence of the test substance, wherein said peptide substrate comprises a fluorescent group and a quencher in sufficient proximity such that the fluorescent group does not emit light from the intact substrate, and wherein the KLK5 protease cleaves the substrate to release the fluorescent group to produce a detectable signal, and wherein an increase in fluorescent signal indicates that said test substance stimulates KLK5 activity.

* * * * *